United States Patent
Kaethner et al.

(10) Patent No.: US 12,257,087 B2
(45) Date of Patent: Mar. 25, 2025

(54) POSITION DETERMINING METHOD, METHOD FOR ACTUATING AN X-RAY DEVICE AND MEDICAL SYSTEM

(71) Applicant: Siemens Healthcare GmbH, Erlangen (DE)

(72) Inventors: Christian Kaethner, Forchheim (DE); Andreas Meyer, Bubenreuth (DE); Michael Wiets, Langensendelbach (DE)

(73) Assignee: Siemens Healthineers AG, Forchheim (DE)

( * ) Notice: Subject to any disclaimer, the term of this patent is extended or adjusted under 35 U.S.C. 154(b) by 745 days.

(21) Appl. No.: 17/409,944

(22) Filed: Aug. 24, 2021

(65) Prior Publication Data
US 2022/0061783 A1    Mar. 3, 2022

(51) Int. Cl.
*A61B 6/00* (2024.01)
*A61B 6/12* (2006.01)
(Continued)

(52) U.S. Cl.
CPC .............. *A61B 6/12* (2013.01); *A61B 6/4441* (2013.01); *A61B 34/30* (2016.02); *G05D 3/20* (2013.01);
(Continued)

(58) Field of Classification Search
CPC ......... A61B 6/12; A61B 6/4441; A61B 34/30; A61B 2034/107; A61B 2034/2065; A61B 2034/303; A61B 2034/301; A61B 6/54; A61B 34/20; A61B 2034/2051; A61B 2090/376; A61B 6/469; A61B 6/5229;
(Continued)

(56) References Cited

U.S. PATENT DOCUMENTS 11,850,008 B2 * 12/2023 Ummalaneni ... A61B 1/000094
2010/0069833 A1    3/2010 Wenderow et al.
2020/0170720 A1    6/2020 Ummalaneni

FOREIGN PATENT DOCUMENTS

EP    3406291 B1    12/2019
WO    2014097086 A1    6/2014

OTHER PUBLICATIONS

German Office Action for German Application No. 10 2020 210 849.8 dated Jun. 21, 2021.

* cited by examiner

*Primary Examiner* — Joel Lamprecht
(74) *Attorney, Agent, or Firm* — Lempia Summerfield Katz LLC

(57) ABSTRACT

Rapid and precise recording of a VOI is provided while monitoring a robot-assisted movement of a medical object through a hollow organ of a patient. For actuating an x-ray device that has a recording system, a user input for the recording of a recording region is accepted. A previously recorded three-dimensional volume image of at least part of the body, in particular of the hollow organ is provided. A length of travel covered by the object from measurement data and/or control data of the robotic system is ascertained. The current position of the object is ascertained on the basis of the three-dimensional volume image making use of the ascertained length of travel covered and a starting position of the object. The recording system of the imaging device is moved for isocentering and/or superimposing the recording region about the current position of the object. An image of the recording region is recorded.

5 Claims, 4 Drawing Sheets

(51) Int. Cl.
*A61B 34/30* (2016.01)
*G05D 3/20* (2006.01)
*G06T 7/00* (2017.01)
*G06T 7/70* (2017.01)
*G06T 15/08* (2011.01)
*A61B 34/10* (2016.01)
*A61B 34/20* (2016.01)
*A61M 25/01* (2006.01)

(52) U.S. Cl.
CPC .............. *G06T 7/0012* (2013.01); *G06T 7/70* (2017.01); *G06T 15/08* (2013.01); *A61B 2034/107* (2016.02); *A61B 2034/2065* (2016.02); *A61B 2034/303* (2016.02); *A61M 2025/0166* (2013.01); *G06T 2200/04* (2013.01); *G06T 2207/30004* (2013.01)

(58) Field of Classification Search
CPC ........ A61B 6/547; G05D 3/20; G06T 7/0012; G06T 7/70; G06T 15/08; G06T 2200/04; G06T 2207/30004; A61M 2025/0166
See application file for complete search history.

POSITION DETERMINING METHOD, METHOD FOR ACTUATING AN X-RAY DEVICE AND MEDICAL SYSTEM

RELATED CASE

This application claims the benefit of German Application 10 2020 210 849.8, filed on Aug. 27, 2020, which is hereby incorporated by reference in its entirety.

FIELD

The present embodiments relate to a method for determining a current position of an object that has been inserted into the body of a patient, a method according for actuating an x-ray device making use of the method for determining the current position of the object, a method according for actuating an x-ray device, and an apparatus.

BACKGROUND

Interventional medical procedures in hollow organs, e.g., the vascular system of the human body, require medical objects, e.g., devices or instruments, to be introduced via a percutaneous vascular access into the vascular system and guided to the target region to be treated. The operator conventionally introduces the objects, e.g., guide catheters, microcatheters or guide wires, into the vascular system via an entry point with the aid of imaging, e.g., radioscopy, and navigates the object into the target region with the aid of an injected contrast medium for visibility of the vessels. The operator, aided by an assistant, in many cases stands directly at the patient table to perform the procedure.

In a development of this medical procedure, a robotic system is connected between the hands of the operator and the patient, with the advantage that the operator no longer has to stand directly at the patient support table, but can perform the maneuvering of the objects (rotational, forward and backward movement) via remote control. Such robotic systems by which (semi)automatic movement of an object, e.g., a catheter and/or guide wire, can be effected in a hollow organ of a patient with the aid of a robot are known in principle, e.g., from EP 3406291 B1. To achieve this, the operator is provided with a corresponding user interface for the remotely controlled movements. It is also advantageous for radioscopic images to be recorded by an imaging device, transferred and displayed to the operator for the required visual feedback. The advantage of this robotic guidance of the medical object lies inter alia in the convenient working position of the operator, the ability to leave the radiation area at the patient table completely, and therefore greater occupational safety as a result of avoiding radiation.

In the case of demanding vascular situations in particular, e.g., in the case of chronic or acute total occlusions, it is beneficial, to achieve a good level of treatment success, for the medical object that is moved in the vessel and its immediate environment in the vessel to be recorded and displayed in 3D. To obtain such a volume image (e.g., a DynaCT image) from an imaging device, a very high x-ray dose is however used when the x-ray window (collimator) is fully open. The prior art discloses a high-resolution so-called VOI (volume of interest) display based on significantly restricting the x-ray window during the 3D routine, i.e., effecting a superimposition on the object and its immediate surroundings. For this purpose, the imaging device and/or the support table must be positioned in such a way that the object is aligned as closely as possible at the isocenter of the recording system (e.g., C-arm) of the imaging device. It is very time consuming to carry out such positioning of the imaging device manually.

SUMMARY AND DESCRIPTION

The object of the present embodiments is to provide a method for actuating a medical system that has an imaging device and a robotic system for moving a medical object. Said method allows isocentering on a VOI to be as quick and precise as possible. The object of the embodiments is further to provide a medical system suitable for performing the method. The object of the embodiments is additionally to provide a method, which is as simple as possible, for determining a current position of an object that has been inserted into the body of a patient.

The object is achieved by a method for determining a current position of an object that has been inserted into the body of a patient, by a method for actuating an x-ray device, by a method for actuating an x-ray device, and by an apparatus. Advantageous embodiments are the subject matter of the associated claims.

By the method for determining a current position of an object that has been inserted into the body, in particular into a hollow organ, of a patient, the object in the body can be moved in a robot-assisted manner by a robotic system. The position of the object can quickly be determined very precisely without having to use additional x-rays. In order to achieve this, the following acts are performed: providing a previously recorded three-dimensional volume image (pre-volume image) of at least part of the body, in particular of the hollow organ, ascertaining a length of travel covered by the object from measurement data and/or control data of the robotic system, and determining and/or calculating the current position of the object on the basis of the three-dimensional volume image making use of the ascertained length of travel covered and the starting position of the object. It is also unnecessary in the method to use a further position determining system such as e.g., a navigation system. The method offers a very simple approach for determining a position, since only the length of travel covered in a longitudinal direction and the starting point of the object are used here to determine the current position.

Robotic systems by which (semi)automatic movement of an object, e.g., a catheter and/or guide wire, can be effected in a hollow organ of a patient with the aid of a robot are known in principle, e.g., from EP 3406291 B1.

According to an embodiment, the robotic system has a drive system with a drive. Said drive system causes the object to advance and measurement data and/or control data of the drive system is used to ascertain the length of travel covered by the object. The drive system, e.g., a stepping motor, can identify e.g., from its control data or by a measurement how many millimeters or centimeters the advance and hence the length of travel of the object already comprises.

According to an embodiment, path planning data that was previously created, in particular on the basis of the three-dimensional volume image (pre-volume image), can be used to determine the position of the object. In particular, the ascertained length of travel covered can be combined with a path that was previously planned for the movement of the object, in order to determine the current position. It is thus possible, e.g., assuming the object has followed the planned path, to display the precise current position in the path planning data. Since the path planning data is generally registered with the coordinate system of the patient, it is also easily possible to determine the current absolute position of the object.

The embodiments further include a method for actuating an x-ray device that has a recording system, making use of the method for determining a current position of an object that has been inserted into a hollow organ of a patient. The object in the body can be moved in a robot-assisted manner by a robotic system. The method includes the following additional acts: automatically moving the recording system of the x-ray device for the purpose of isocentering and/or superimposing a recording region which includes the current position of the object, and recording an image of the recording region, in particular in the form of a collimated volume image, e.g., a VOI. In this context therefore, based on the determination of the current position of the object, the recording system of the x-ray device is actuated and moved in such a way that the current position of the object is situated at the isocenter of the recording system and an additional superimposition is performed if necessary. The VOI thus obtained is then recorded automatically by a 3D recording, e.g., DynaCT. The method can be performed automatically in a particularly quick and easy manner using a low x-ray dose. It is therefore possible to display high-quality recordings of the required recording region without unnecessarily exposing the patient to additional radiation. By virtue of the high-quality recordings, a particularly good diagnostic opinion and improved treatment success can be achieved.

To ensure particularly smooth execution of the method, the x-ray device is advantageously registered in advance with the at least one previously recorded three-dimensional volume image and/or path planning data.

According to a further embodiment, provision can be made for accepting a user input that initiates the method for actuating. The user input can be used as a trigger for the method, which e.g., a doctor can start as required.

According to a further embodiment, the x-ray device has a patient table and the patient table is also moved for the purpose of isocentering and/or superimposing the recording region.

The embodiments further include a method for actuating an x-ray device that has a recording system, while monitoring a robot-assisted movement, performed by a robotic system, of a medical object through a hollow organ of a patient. The method includes the following acts: accepting a user input for the recording of a recording region, providing a previously recorded three-dimensional volume image of at least part of the body, in particular of the hollow organ, ascertaining a length of travel covered by the object from measurement data and/or control data of the robotic system, determining and/or calculating the current position of the object on the basis of the three-dimensional volume image making use of the ascertained length of travel covered and the starting position of the object, automatically moving the recording system of the x-ray device for the purpose of isocentering and/or superimposing the recording region which includes the current position of the object, and recording an image of the recording region, in particular in the form of a collimated volume image, e.g., a VOI. By virtue of the method, the position of the object can quickly be determined very precisely without having to use additional x-rays.

The method offers a very simple arrangement for determining a position, since only the length of travel covered in a longitudinal direction and the starting point of the object are used here to determine the current position. Based on the position determination, the recording system of the x-ray device is then actuated and moved in such a way that the current position of the object is situated at the isocenter of the recording system and an additional superimposition is performed if necessary. The VOI thus obtained is then recorded automatically by a 3D recording, e.g., DynaCT. The method can be performed automatically in a particularly quick and easy manner using a low x-ray dose. It is therefore possible to display high-quality recordings of the required recording region without unnecessarily exposing the patient to additional radiation. By virtue of the high-quality recordings, a particularly good diagnostic opinion and improved treatment success can be achieved.

The embodiments further include a medical system, having a robotic system with at least a robot control unit and a robot-assisted drive system including a drive and a drive mechanism. The drive system is configured to move a medical object in a hollow cavity organ of a patient by control signals from the robot control unit on the basis of path planning data. A controller or a calculation unit (calculator or processor) is configured to ascertain a length of travel covered by the object from measurement data and/or control data of the drive system and to determine and/or calculate the current position of the object on the basis of a three-dimensional volume image using the ascertained length of travel covered and the starting position of the object. An x-ray device with a system control unit (controller) and a movable recording system is provided for recording images of a recording region that can be depicted. The system control unit is configured to actuate the recording system for the purpose of movement and image recording in such a way that automatic movement of the recording system takes place for the purpose of isocentering and/or superimposing the recording region that includes the current position of the object, and that an image recording of the recording region is performed, in particular in the form of an enlarged volume image. An input unit or device is provided for accepting a user input. In particular, the recording system takes the form of a C-arm. The medical system can also have a movable patient table.

BRIEF DESCRIPTION OF THE DRAWINGS

The invention and further advantageous embodiments as per features in the subclaims are explained in greater detail below with reference to schematically illustrated exemplary embodiments in the drawings, without thereby restricting the invention to these exemplary embodiments.

DETAILED DESCRIPTION OF THE PREFERRED EMBODIMENTS

Figure 1:
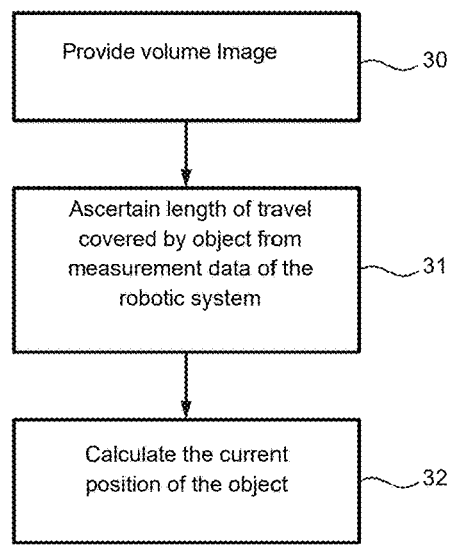
FIG. 1 shows one embodiment of a sequence of a method for determining a current position of an object that has been inserted into the body of a patient.

FIG. 1 shows acts of a method for determining a current position of an object that has been inserted into the body, in particular into a hollow organ (i.e., a vascular system, vascular tree, bronchial system, etc., for example), of a patient, which object can be moved through the hollow organ in a robot-assisted manner by a robotic system. Robotic systems by which (semi)automatic movement of an object, e.g., a catheter, stent and/or guide wire, can be effected in a hollow organ of a patient with the aid of a robot are known in principle, e.g., from EP 3406291 B1. After some time during which the object has been moved, it becomes necessary for e.g., an operator (e.g., a doctor) to check the position or determine the current position.

In a first act 30, a previously recorded three-dimensional volume image ("pre-op") of at least part of the body, in particular the hollow organ, is provided. Such volume images are generally prepared to obtain an overview of the entire treatment region and in order to allow, e.g., path planning to be performed for the movement of the object. The previously recorded volume image is or was previously registered with e.g., the coordinate system of the patient. Such a volume image may have been prepared by e.g., a CT, an MR or an angiography x-ray device.

In a second act 31, the length of travel already covered by the object as a result of the robot-assisted advance is ascertained from measurement data and/or control data of the robotic system. For example, the data of a stepping motor that causes the advance can be retrieved and used here. The data can be processed and converted accordingly to obtain the length of travel covered. However, only the distance can generally be ascertained from the length of travel covered, not the exact path or the exact position.

Figure 3:
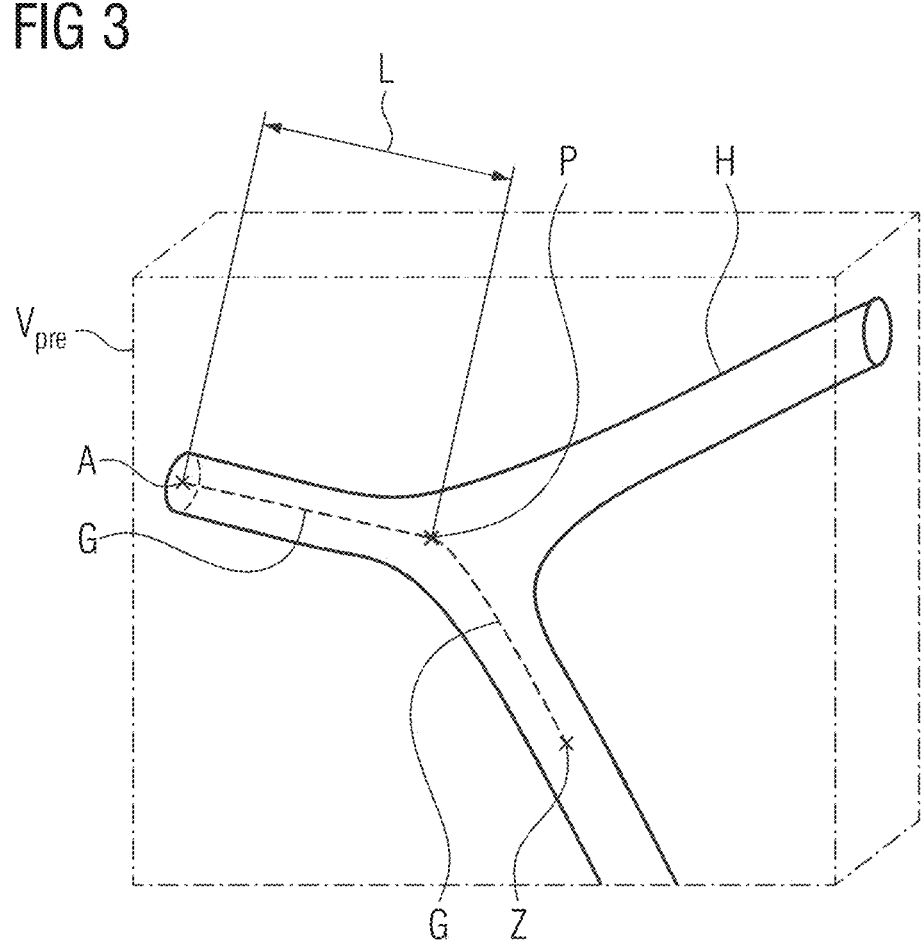
FIG. 3 shows an example view of a current position of an object, calculated on the basis of a volume image.
Figure 4:
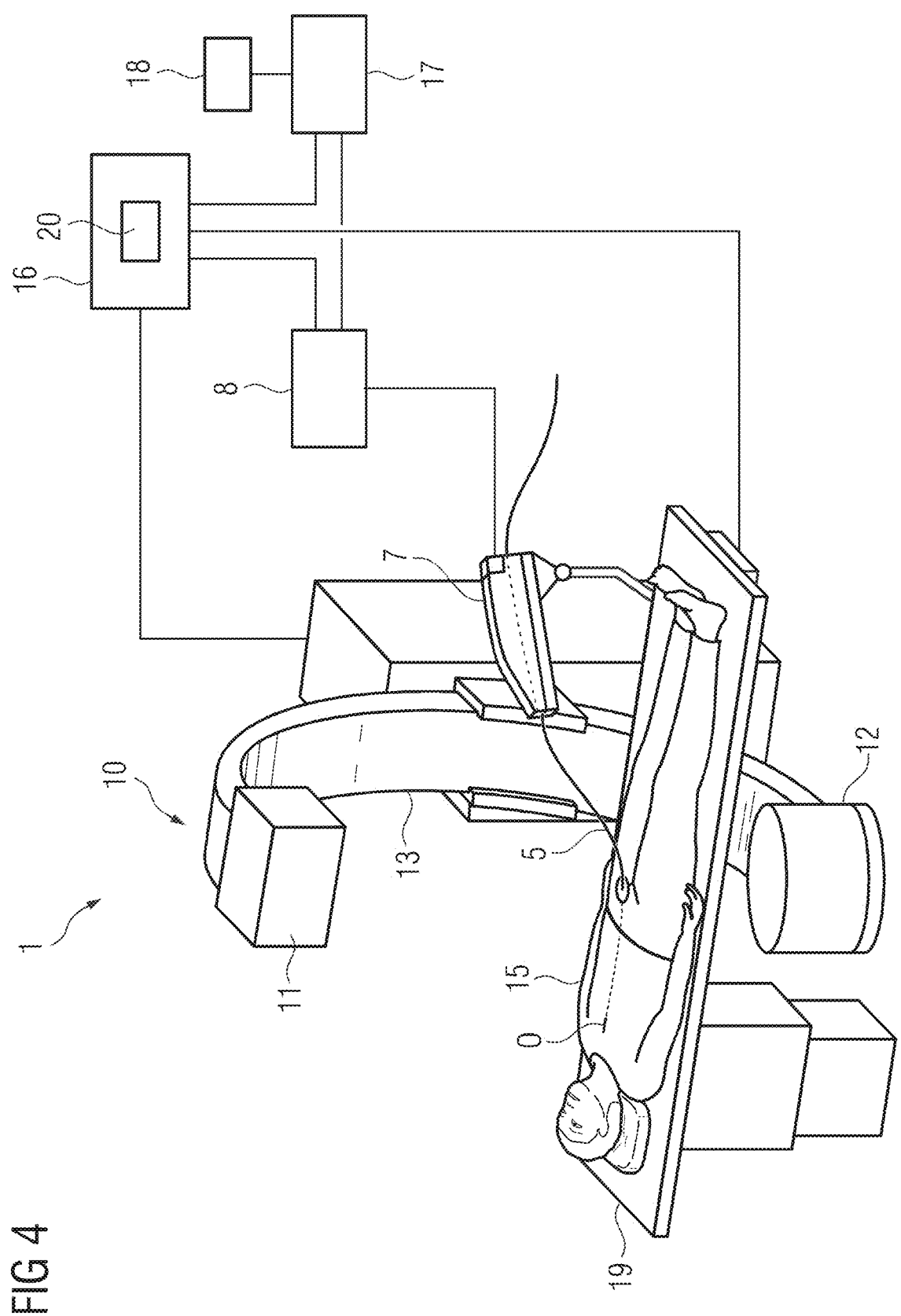
FIG. 4 shows an example view of a medical system.

Therefore, in a third act 32, the current position of the object is then ascertained or calculated on the basis of the three-dimensional volume image, making use of the ascertained length of travel covered and the starting position of the object. For the purpose of illustration, FIG. 3 shows the previously created volume image $V_{pre}$ with the hollow organ H depicted therein. The previously planned path G for the travel of the object O is shown in the previously created volume image $V_{pre}$. Starting from the starting position A of the object, the length of travel L covered is then applied to the planned path G and the current position P of the object O is thereby obtained very precisely. This can also be performed without a path plan and on the basis of the previously created volume image $V_{pre}$ alone. To be able to retrace the course that was actually followed e.g., at branch points of the hollow organ, and for approximate orientation, information from fluoroscopy recordings or data from other navigation systems can also be used here.

Figure 2:
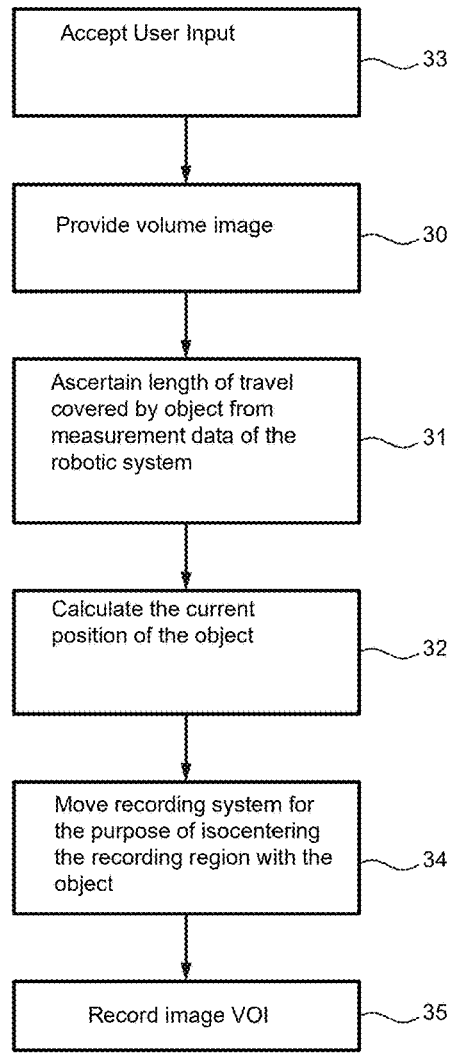
FIG. 2 shows one embodiment of a sequence of a method for actuating an x-ray device while monitoring a robot-assisted movement of a medical object through a hollow organ of a patient.
Figure 5:
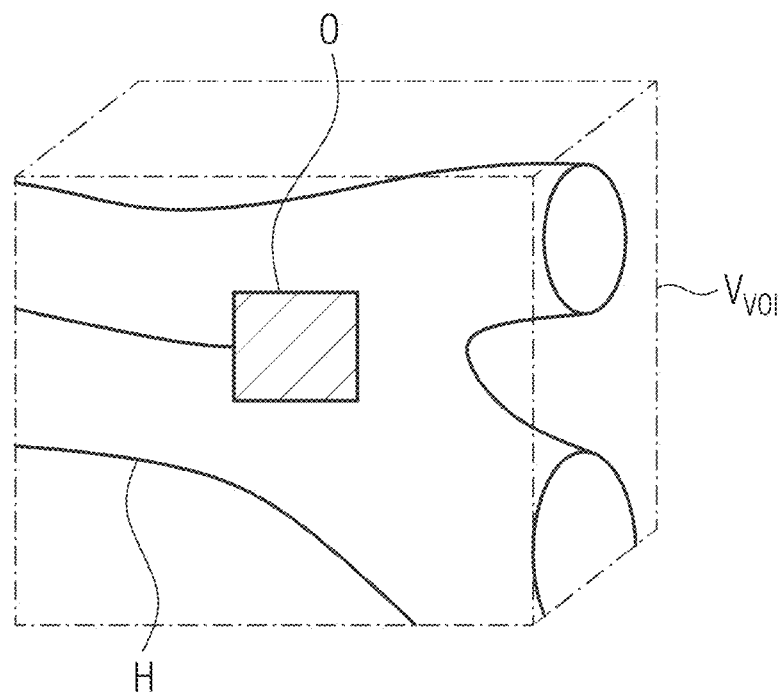
FIG. 5 shows an example view of a VOI volume image recorded by the method.

FIG. 2 shows a sequence of a method for actuating an x-ray device, which method uses the position determining method according to FIG. 1. For example, a medical system 1 as shown in FIG. 5 is used for this. The medical system 1 has a robotic system and an x-ray device 10. The robotic system is configured for semiautomatic or automatic movement of the medical object O, e.g., an instrument, stent, guide wire or catheter, in a hollow organ of a patient 15. A semiautomatic actuation in this case is understood to mean e.g., an actuation that can be transferred from an operator via an input unit 17 (e.g., joystick, touchpad, rotary switch, etc.) to a robot control unit 8. The robotic system has at least a robot control unit (controller) 8 and a robot-assisted drive system 7. The drive system 7 is configured to move the medical object e.g., in the hollow organ of the patient 15 based on control signals from the robot control unit 8 after it has been introduced at an entry point. The drive system 7 in this case includes at least a drive and a drive mechanism (not shown, e.g., disclosed in EP 3406291 B1), said drive mechanism being separably coupled to the guide wire 5, for example. By the drive mechanism and the drive, the guide wire 5 can be advanced and withdrawn longitudinally and/or additionally moved in a rotary manner. The length of travel of the longitudinal advance can be determined from measurement data or control data of the drive system (e.g., a stepping motor). The robot control unit 8 is connected to an input unit (input device) 17 (e.g., arranged remotely from the patient) which can be operated by an operator, e.g., a cardiologist or radiologist performing the intervention. The control signals are transferred from the input unit 17 (e.g., one or more joysticks, touchpads, control buttons, etc.) to the robot control unit 8, and in this way the movements of the object are semiautomatically actuated. Alternatively, the operator can also carry out path planning for the object or have a path plan created automatically. This is transferred to the robot control unit 8, whereby movement can take place completely automatically. The path plan can also be used as a reference in the case of semiautomatic movement.

To have an overview of the intervention and the movement, the x-ray device 10 is provided. The x-ray device 10 has e.g., a C-arm 13 which supports an x-ray source 12 and an x-ray detector 11 and is connected to a system control unit 16. The C-arm 13 is so arranged as to be movable relative to the patient, and the whole x-ray device can be moved in the case of a mobile x-ray device. Alternatively or additionally, the patient table 19 can also be moved relative to the x-ray device or recording system. The x-ray device 10 makes it possible to create images of a recording region that can be depicted and display said images on a display unit (display screen) 18. The robot control unit 8 and the system control unit (controller) 16 of the imaging device can exchange data bidirectionally and communicate with each other. It is also possible to provide a combined control unit (controller) including the robot control unit 8 and the system control unit 16. The medical system 1 also includes a calculation unit (calculator, controller, or processor) 20, which is configured to ascertain a length of travel covered by the object from measurement data and/or control data of the drive system and to determine and/or calculate the current position of the object on the basis of the previously created volume image making use of the ascertained length of travel covered and the starting position of the object. Registration of the robotic system with the x-ray device can be performed in advance, e.g., using previously created 3D image data.

If an operator requires a precise 3D representation of the object and its environment, e.g., in the vicinity of a vascular branch point, in the form of a VOI recording, the operator performs a user input. The user input is accepted by e.g., the system control unit 16 (fourth act 33) and this acceptance triggers the method; see FIG. 2. In a first act 30, a previously recorded three-dimensional volume image ("pre-op") $V_{pre}$ of at least part of the body, in particular the hollow organ, is then provided. The previously recorded volume image is or was previously registered with e.g., the coordinate system of the x-ray device (or already directly created by this). In a second act 31, the length of travel already covered by the object as a result of the robot-assisted advance is ascertained from measurement data and/or control data of the robotic system. For example, the data of a stepping motor which causes the advance can be retrieved and used here. The data can be processed and converted accordingly to obtain the length of travel covered. However, only the distance can generally be ascertained from the length of travel covered, and not the exact path. Therefore, in a third act 32, the current position of the object is then ascertained or calculated on the basis of the three-dimensional volume image, making use of the ascertained length of travel covered and the starting position of the object. Once the current position of the object has been ascertained, it is forwarded to the system control unit 16 of the x-ray device 1 for the actuation and, in a fifth act 34, the recording system of the x-ray device (and/or the patient table 19) is moved automatically such that isocentering of the current position of the object is achieved. In particular, the object becomes the central point of the recording region. Furthermore, a superimposition (e.g., by a collimator) is also performed, so that only the object and its immediate environment, i.e., the VOI, are superimposed. The precise dimensioning of the VOI can be preset or selected automatically. This may represent e.g., a quarter or less of the volume of a complete image. Finally, in a sixth act 35, a VOI volume image $V_{VOI}$ of the superimposed recording region is recorded with the object O and its immediate environment; see FIG. 5. By virtue of such a VOI volume image, it is possible more effectively to identify e.g., critical situations during movement of the object (e.g., in the case of vascular branch points or vascular occlusions) and therefore to achieve a better diagnostic opinion and treatment. As a result of automating the method, it is possible to perform an image recording quickly and effortlessly.

The method can be made even more resilient by sensor technology, e.g., a navigation system, for the tip or the central point (in the case of stents) of the object, e.g., EM tracking.

The advantage of the proposed method lies in the automation of the resource-intensive positioning of the recording system (and possibly the patient table). In this way, it is possible to generate a VOI volume image, i.e., a significantly smaller volume image in respect of the x-ray window, of the desired recording region, i.e., the object and its immediate environment. By virtue of the smaller image region, the x-ray dose is significantly reduced and therefore the risk to the patient is minimized in comparison with a full-format 3D recording.

The embodiments can be briefly summarized as follows: for a particularly rapid and precise recording of a VOI while monitoring a robot-assisted movement, performed by a robotic system, of a medical object through a hollow organ of a patient, a method including the following acts is provided for the purpose of actuating an x-ray device that has a recording system: accepting a user input for the recording of a recording region, providing a previously recorded three-dimensional volume image of at least part of the body, in particular of the hollow organ, ascertaining a length of travel covered by the object from measurement data and/or control data of the robotic system, determining and/or calculating the current position of the object on the basis of the three-dimensional volume image making use of the ascertained length of travel covered and the starting position of the object, automatically moving the recording system of the imaging device for the purpose of isocentering and/or superimposing the recording region which includes the current position of the object, recording an image of the recording region, in particular in the form of a VOI volume image.

It is intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A method for determining a current position of an object that has been inserted into a hollow organ of a patient, wherein the object is moved by a drive mechanism of a robotic system, the method comprising:

acquiring a previously recorded three-dimensional volume image of at least part of the hollow organ comprising at least a starting position of the object, acquiring path planning data that was created previously based on the previously recorded three-dimensional volume image, ascertaining, in the previously recorded three-dimensional volume image, a length of travel covered by the object from measurement data and/or control data of the robotic system, determining and/or calculating the current position of the object using the ascertained length of travel covered, the path planning data, and the starting position of the object, automatically actuating, by a system control unit of an x-ray device, a recording system of the x-ray device so that the current position of the object is situated at the isocenter of the recording system and/or a recording region of the recording system is superimposed at the current position of the object, and recording a recording region image of the recording region.

2. The method as claimed in claim 1, wherein the robotic system has a drive system which comprises a drive and causes the object to advance, and wherein measurement data and/or control data of the drive system is used to ascertain the length of travel covered by the object.

3. The method as claimed in claim 1, wherein the x-ray device is registered in advance with the at least one previously recorded three-dimensional volume image and/or the path planning data.

4. The method as claimed in claim 1, wherein a user input is accepted which triggers the method.

5. The method as claimed in claim 1, wherein the x-ray system has a patient table and wherein the patient table is also moved to isocenter and/or superimpose the recording region.

* * * * *

UNITED STATES PATENT AND TRADEMARK OFFICE
CERTIFICATE OF CORRECTION

| | | |
|---|---|---|
| PATENT NO. | : 12,257,087 B2 | Page 1 of 1 |
| APPLICATION NO. | : 17/409944 | |
| DATED | : March 25, 2025 | |
| INVENTOR(S) | : Christian Kaethner | |

It is certified that error appears in the above-identified patent and that said Letters Patent is hereby corrected as shown below:

On the Title Page

Add item (30) to read:
Foreign Application Priority Data Aug. 27, 2020 (DE) ............... 10 2020 210 849.8

Signed and Sealed this
Sixteenth Day of September, 2025

Coke Morgan Stewart
*Acting Director of the United States Patent and Trademark Office*